United States Patent
Berdahl et al.

(10) Patent No.: US 10,179,136 B2
(45) Date of Patent: *Jan. 15, 2019

(54) PHARMACEUTICAL COMPOSITIONS AND METHODS FOR ANESTHESIOLOGICAL APPLICATIONS

(71) Applicant: IMPRIMIS PHARMACEUTICALS, INC., San Diego, CA (US)

(72) Inventors: John Berdahl, Sioux Falls, SD (US); William F. Wiley, Chagrin Falls, OH (US); Dennis Elias Saadeh, Irvine, CA (US)

(73) Assignee: Imprimis Pharmaceuticals, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/903,615

(22) Filed: Feb. 23, 2018

(65) Prior Publication Data

US 2018/0177797 A1   Jun. 28, 2018

Related U.S. Application Data

(63) Continuation-in-part of application No. 15/184,768, filed on Jun. 16, 2016, now Pat. No. 9,918,993.

(60) Provisional application No. 62/182,130, filed on Jun. 19, 2015.

(51) Int. Cl.
| | | |
|---|---|---|
| A61K 31/138 | (2006.01) | |
| A61K 31/5517 | (2006.01) | |
| A61K 9/20 | (2006.01) | |
| A61K 45/06 | (2006.01) | |
| A61P 23/00 | (2006.01) | |
| A61K 9/00 | (2006.01) | |

(52) U.S. Cl.
CPC ........ *A61K 31/5517* (2013.01); *A61K 9/0056* (2013.01); *A61K 9/2031* (2013.01); *A61K 31/138* (2013.01); *A61K 45/06* (2013.01); *A61P 23/00* (2018.01); *A61K 2300/00* (2013.01)

(58) Field of Classification Search
CPC .............. A61K 31/5517; A61K 9/0056; A61K 31/138; A61K 31/135
See application file for complete search history.

(56) References Cited

U.S. PATENT DOCUMENTS

| 4,246,894 A | 1/1981 | Hamacher |
|---|---|---|
| 9,918,993 B2 * | 3/2018 | Berdahl ............ A61K 31/5517 |
| 2007/0116764 A1 | 5/2007 | Marunaka et al. |
| 2009/0175939 A1 | 7/2009 | Bosse et al. |
| 2013/0345202 A1 | 12/2013 | Amselem |
| 2014/0079740 A1 | 3/2014 | Salama |
| 2018/0177796 A1 | 6/2018 | Berdahl et al. |
| 2018/0271877 A1 | 9/2018 | Berdahl et al. |

FOREIGN PATENT DOCUMENTS

| WO | 95/22965 A2 | 8/1995 |
|---|---|---|
| WO | 96/25925 A1 | 8/1996 |

OTHER PUBLICATIONS

PCT/US2016/037893 International Search Report and Written Opinion dated Sep. 7, 2016.
Chia et al. "Role of β-blockade in anaesthesia and postoperative pain management after hysterectomy," British Journal of Anaesthesia, 2004, 93(6):799-805.
Davis et al. "Effect of Antiemetic Therapy on Recovery and Hospital Discharge Time." Anesthesiology, 1995, 83:956-960.
Ramaiah et al. "Pediatric procedural sedation and analgesia outside the operating room: anticipating, avoiding and managing complications," Expert Rev. Neurother, 2011, 11(5):755-763.
Tobias et al. "Procedural sedation: A review of sedative agents, monitoring, and management of complications," Saudi J Anaesth., 2011, 5(4):395-410.
Mclean et al. "The pharmacological treatment of nystagmus: a review," Expert Opinion on Pharmacotherapy, 2009, 10(11):1805-1816.
Macdonald et al. "Central Positional Nystagmus: A Systematic Literature Review," Frontiers in Neurology, Apr. 2017, 8:1-11.
JP2017-566010 Office Action dated Jun. 5, 2018.
KR10-2018-7000815 Office Action dated Aug. 2, 2018.

* cited by examiner

*Primary Examiner* — Sudhakar Katakam
(74) *Attorney, Agent, or Firm* — Wagenknecht IP Law Group PC

(57) ABSTRACT

Pharmaceutical compositions and methods for inducing conscious sedation using such compositions are described, the compositions including a benzodiazepine-based compound, a NMDA antagonist, and optionally a β-blocker, antiemetic, an NSAID, and/or an antihistamine medication. Methods for fabricating the compositions and using them for anesthesiological applications are also described.

23 Claims, No Drawings

PHARMACEUTICAL COMPOSITIONS AND METHODS FOR ANESTHESIOLOGICAL APPLICATIONS

CROSS REFERENCE TO RELATED APPLICATION(S)

This is a continuation-in-part patent application under 35 U.S.C. § 120 to U.S. patent application Ser. No. 15/184,768, filed Jun. 16, 2016, now pending, which in turn claims the benefit of priority under 35 U.S.C. § 119(e) of U.S. Provisional Application No. 62/182,130, filed Jun. 19, 2015, the entire content of each of which is incorporated herein by reference.

FIELD OF THE INVENTION

The present invention relates generally to the field of pharmacology and more specifically to compositions having anesthetic properties that are useful in various kinds of surgery, e.g., ophthalmic surgery, and to methods of preparing and using such compositions.

BACKGROUND

The present disclosure relates to solid or liquid pharmaceutical formulations comprising combinations of active agents such as anesthetics, anti-emetics, blood pressure, anti-anxiety medications and/or analgesics, and methods for using the same for providing anesthesia by administering such compositions orally, e.g., sublingually or bucally. The formulations may also include slow release reversal agents that would counteract the initial anesthesia effect.

It is necessary in many cases to use local anesthesia, particularly via oral route in the course of various surgical procedures, e.g., ophthalmic surgeries or urological interventions. For instance, when local anesthesia is employed during or prior to intraocular operations, the occurrences of pain, anxiety, peri-operative stress, nausea, agitation, vomiting and the like are less frequent, which will typically have a very beneficial effect on the surgical experience and reducing the number of intraocular complications such as bleeding, secretions, cardiac and/or pulmonary complications, etc. The severity of those complications when they do occur will also be less pronounced when local anesthesia is used.

Traditionally intravenous route is used to administer medications. Alternatives to intravenous methods and therapies have been suggested and previously used for the treatment. In particular, oral administration of benzodiazepines, opioid analgesics, propofol, ketamine or etomidate utilizing the MAC procedure (monitored anesthesia care) has been suggested and tried, but no more than minimal to moderate improvement has been achieved by such methods. Therefore, there remains a need for better treatments of these disorders.

This patent specification discloses such pharmaceutical compositions suitable for anesthesiological applications that can achieve positive patient outcomes while free of drawbacks and deficiencies of existing methods and formulations. Methods of fabricating and administering the same are also discussed.

SUMMARY

According to one embodiment of the invention, there are provided pharmaceutical compositions. The compositions include a therapeutically effective quantity of at least one first pharmaceutically active compound comprising benzodiazepine moiety or pharmaceutically acceptable salts, hydrates, solvates or N-oxides thereof, a therapeutically effective quantity of at least one second pharmaceutically active compound that is an NMDA antagonist or pharmaceutically acceptable salts, hydrates, solvates or N-oxides thereof, and at least one pharmaceutically acceptable excipient or carrier therefor.

According to another embodiment of the invention, the pharmaceutical compositions described above may further include a therapeutically effective quantity of at least one third pharmaceutically active compound that is a β-blocker, a nonsteroidal anti-inflammatory drug (NSAID), or an anti-emetic medicament, or a combination thereof, or pharmaceutically acceptable salts, hydrates, solvates or N-oxides thereof.

According to further embodiments of the invention, in the pharmaceutical compositions described above, the first pharmaceutically active compound may be any of midazolam, diazepam, lorazepam, flunitrazepam, alprazolam, chlordiazepoxide, clonazepam or clorazepate, the second pharmaceutically active compound may be any of ketamine, dextrorphan, etomidate, methadone, memantine, amantadine or dextromethorphan and the third pharmaceutically active compound may be (if a β-blocker) any of metoprolol, propranolol, acebutolol, nadolol, atenolol, betaxolol, esmolol, bisoprolol fumarate, carvedilol, nebivolol, penbutolol, timolol, or sotalol or (if an antiemetic) ondansentron, dolasetron, granisetron, palonosetron, promethazine, imenhydrinate, or meclizine.

According to yet another embodiment of the invention, there are provided further pharmaceutical compositions such as any described above, wherein the compositions are formulated as a liquid or a solid item, e.g., a troche, a lozenge, a capsule, a pill, a cap and a bolus suitable for sublingual or oral administration.

According to other embodiments, there are provided specific compounds for making the compositions described above, for example, midazolam, ketamine and ondansetron, as well as methods for using above-mentioned composition(s) for the purposes of local anesthesia in various applications, such as ophthalmic surgery.

According to further embodiments of the invention, the above-mentioned methods of using the composition(s) include orally administering to a patient in need thereof (i.e., those patients who require conscious sedation or pre-sedation) a pharmaceutical composition described herein as the first step of a medical or surgical procedure, the procedure being an ophthalmic surgery (e.g., a cataract, glaucoma, corneal, eyelid surgery, or retinal surgery), a dental procedure (e.g., a tooth extraction, an oral surgery, or a root canal surgery), an outpatient medical procedure (e.g., medical imaging procedure, biopsy, bone marrow harvesting, colonoscopy, or endoscopy), a urological procedure, a laparoscopic procedure, obstetric and gynecological procedures, a gastrointestinal procedure, an otolaryngological procedure, a cosmetic surgery procedure, a dermatological procedure, a podiatric procedure, an orthopedic procedure, an emergency medical treatment, a psychiatric treatment, or a veterinarian procedure.

DETAILED DESCRIPTION

A. Terms and Definitions

Unless specific definitions are provided, the nomenclatures utilized in connection with, and the laboratory procedures and techniques of analytical chemistry, synthetic organic and inorganic chemistry described herein, are those known in the art. Standard chemical symbols are used interchangeably with the full names represented by such symbols. Thus, for example, the terms "hydrogen" and "H" are understood to have identical meaning. Standard techniques may be used for chemical syntheses, chemical analyses, formulating compositions and testing them. The foregoing techniques and procedures can be generally performed according to conventional methods well known in the art.

It is to be understood that both the foregoing general description and the following detailed description are exemplary and explanatory only and are not restrictive of the invention claimed. As used herein, the use of the singular includes the plural unless specifically stated otherwise. The section headings used herein are for organizational purposes only and are not to be construed as limiting the subject matter described.

As used herein, "or" means "and/or" unless stated otherwise. Furthermore, use of the term "including" as well as other forms, such as "includes," and "included," is not limiting.

"About" as used herein means that a number referred to as "about" comprises the recited number plus or minus 1-10% of that recited number. For example, "about" 100 degrees can mean 95-105 degrees or as few as 99-101 degrees depending on the context. Whenever it appears herein, a numerical range such as "1 to 20" refers to each integer in the given range; i.e., meaning only 1, only 2, only 3, etc., up to and including only 20.

The term "pharmaceutical composition" is defined as a chemical or biological compound or substance, or a mixture or combination of two or more such compounds or substances, intended for use in the medical diagnosis, cure, treatment, or prevention of disease or pathology.

The terms "anesthetic," "anesthesia," "anesthesiology" and the like refer herein to substances, compounds, processes or procedures that induce insensitivity to pain such as a temporary loss of sensation.

The term "conscious sedation" that for the purposes of this application may be used interchangeably with terms "procedural sedation" and "analgesia" is used herein to refer to an induced state of sedation characterized by a minimally depressed consciousness such that the patient is able to continuously and independently maintain a patent airway, retain protective reflexes, and remain responsive to verbal cues and/or tactile or physical stimulation.

Conscious sedation is typically performed/induced to decrease the level of anxiety in a patient and to elicit an improved degree of cooperation from the patient prior to or during a procedure. Conscious sedation, therefore, refers to a condition that is medically different and distinct from deep sedation which is the next level of sedation defined as depression of consciousness when the patient's ability to independently maintain ventilatory function may be impaired and he or she cannot be easily aroused; however, the patient will still purposefully respond to repeated or painful stimulation.

Conscious sedation is also clearly distinguishable for the purposes of the present application from the lower level of sedation (i.e., minimal sedation when the patient is able to maintain a normal response to verbal stimuli) as well as the highest level of sedation (i.e., general anesthesia when there is no response from the patient even with painful stimulus).

The term "pre-sedation" is defined for the purposes of this application as conscious sedation that is induced some time before a procedure, e.g, between 5 minutes and 1 hour prior.

The terms "solvate" and "hydrate" are used herein to indicate that a compound or substance is physically or chemically associated with a solvent for "solvates" such as water (for "hydrates").

The term "NMDA antagonist" is defined as a compound that inhibits ("antagonizes") the action of the N-methyl-D-aspartate receptors and is inclusive of both competitive and non-competitive antagonists, glycine antagonists and uncompetitive channel blockers, as these terms are understood by those having ordinary skill in the art.

The term "β-blocker" refers to a compound of any kind that can prevent or reduce the stimulation of the adrenergic receptors responsible for increased cardiac action.

The term "antiemetic" is defined as a drug or medicament that treats, reduces, and/or prevents nausea and/or vomiting.

The term "non-steroid anti-inflammatory drug" or "NSAID" refers to a class of compounds that are free of any steroid moieties yet are capable of providing analgesic, antipyretic and/or anti-inflammatory effects.

The term "antihistamine medicament" refers to any compound that is capable of inhibiting or counteracting the physiological effects of histamine.

The term "polyglycol" is defined as a polymer or oligomer containing several ether-glycol linkages that yields one or more glycols when these linkages are cleaved, e.g., by hydrolysis.

The term "carrier" refers to a substance that serves as a vehicle for improving the efficiency of delivery and the effectiveness of a pharmaceutical composition.

The term "excipient" refers to a pharmacologically inactive substance that is formulated in combination with the pharmacologically active ingredient of pharmaceutical composition and is inclusive of bulking agents, fillers, diluents and products used for facilitating drug absorption or solubility or for other pharmacokinetic considerations.

The term "binder" refers to a substance or compound that promotes, provides or improves cohesion, i.e., a substance that causes the components of a mixture to cohere to form a solid item that possesses integrity.

The term "troche" refers to a small tablet or lozenge (i.e., a medicated candy intended to be dissolved in the mouth), typically in a form of a disk, a ball or rhombic in cross-section, comprising medication and processed into a paste and dried.

The term "therapeutically effective amount" is defined as the amount of the compound or pharmaceutical composition that will elicit the biological or medical response of a tissue, system, animal or human that is being sought by the researcher, medical doctor or other clinician.

The term "pharmaceutically acceptable" when used in the context of a carrier, diluent or excipient, refers to a substance that is compatible with the other ingredients of the formulation and not deleterious to the recipient thereof.

The terms "administration of a composition" or "administering a composition" is defined to include an act of providing a compound of the invention or pharmaceutical composition to the subject in need of treatment.

The terms "oral administration" and "orally administering" are broadly defined as a route of administration where a medication is taken through the mouth including "sublingual administration" and "buccal administration" where the medication is placed under the tongue or between the gums and the cheek, respectively, to be absorbed by the body, or to be administered sublingually or buccally as a liquid.

B. Embodiments of the Invention

According to embodiments of the present invention, there are provided pharmaceutical compositions for anesthetic purposes. The compositions comprise, consist of or consist essentially of, a combination of therapeutically effective quantities of at least one first pharmaceutically active compound and at least one second pharmaceutically active compound. In some further embodiments, the compositions optionally comprise, in addition to the above-mentioned first clobazam, bromazepam, prazepam, oxazepam and clorazepate. Each of these is also known under one or several trade names as shown in Table 1, which also discloses chemical names of such compounds. Those having ordinary skill in the art can select alternative suitable benzodiazepine-based compound for using in the compositions, if so desired.

TABLE 1

Examples of Benzodiazepine-Based Compounds That Can Be Used in Compositions

| Compound | Chemical Name (IUPAC) | Trade Name(s) |
|---|---|---|
| Midazolam | 8-chloro-6-(2-fluorophenyl)-1-methyl-4H-imidazo[1,5-a][1,4]benzodiazepine | VERSED ®, DORMICUM ®, HYPNOVEL ® |
| Diazepam | 7-chloro-1-methyl-5-phenyl-3H-1,4-benzodiazepin-2-one | VALIUM ®, DIASTAT ® |
| Lorazepam | 7-chloro-5-(2-chlorophenyl)-3-hydroxy-1,3-dihydro-2H-1,4-benzodiazepin-2-one | TEMESTA ®, ATIVAN ®, ORFIDAL ® |
| Flunitrazepam | 5-(2-fluorophenyl)-1-methyl-7-nitro-1H-benzo[e][1,4]diazepin-2(3H)-one | ROHYPNOL ®, NARCOZEP ® and many others |
| Alprazolam | 8-chloro-1-methyl-6-phenyl-4H-[1,2,4]triazolo[4,3-a][1,4]benzodiazepine | XANAX ® |
| Chlordiazepoxide | 7-chloro-2-methylamino-5-phenyl-3H-1,4-benzodiazepine-4-oxide | LIBRIUM ® |
| Clonazepam | 5-(2-chlorophenyl)-7-nitro-2,3-dihydro-1,4-benzodiazepin-2-one | KLONOPIN ®, RIVOTRIL ® and many others |
| Clorazepate | 7-chloro-2,3-dihydro-2-oxo-5-phenyl-1H-1,4-benzodiazepine-3-carboxylic acid | TRANXENE ® |
| Bromazepam | 7-bromo-5-(pyridin-2-yl)-1H-benzo[e][1,4]diazepin-2(3H)-one | LEXOTAN ®, LEXOTANIL ® and many others |
| Oxazepam | 7-chloro-3-hydroxy-5-phenyl-2,3-dihydro-1H-1,4-benzodiazepine-2-one | ALEPAM ®, SERAX ® and many others |
| Clobazam | 7-chloro-1-methyl-5-phenyl-1,5-benzodiazepine-2,4(3H)-dione | URBANOL ®, FRISIUM ®, ONFI ® |
| Prazepam | 7-chloro-1-(cyclopropylmethyl)-5-phenyl-1,3-dihydro-2H-1,4-benzodiazepin-2-one | LYSANXIA ®, CENTRAX ® and many others | and second pharmaceutically active compounds, at least one third pharmaceutically active compound.

The first pharmaceutically active compound that is used in such composition comprises a benzodiazepine moiety or pharmaceutically acceptable salts, hydrates, solvates or N-oxides thereof. Those having ordinary skill in the art will know that benzodiazepine moiety is a structure where a benzene ring is condensed with diazepine ring, a seven-member heterocycle with two nitrogen atoms which for the purposes of this specification may be in any positions of the ring (e.g., 1,2-diazepine, 1,3-diazepine or 1,4-diazepine). An example of a compound having benzodiazepine moiety with 1,4-diazepine structure is shown below:

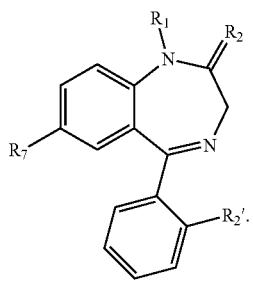

One particular first pharmaceutically active compound comprising a benzodiazepine moiety that can be used in pharmaceutical compositions described and claimed herein is midazolam. Other specific, non-limiting examples of first pharmaceutically active compounds comprising benzodiazepine moiety that can be used include diazepam, lorazepam, flunitrazepam, alprazolam, chlordiazepoxide, clonazepam, The therapeutically effective quantity of the benzodiazepine-based compound(s) in the entire pharmaceutical composition can be between about 0.2 mass % and about 5.0 mass % of the composition. In some embodiments, the therapeutically effective amount of the benzodiazepine-based compound(s) can be between about 1.0 mass % and about 3.0 mass %, for example, about 2.5 mass % of the composition.

In some applications a patient may be extra sensitive to benzodiazepines (e.g., may become excessively drowsy). For such patients, there are provided additional embodiments of the composition in which benzodiazepine(s)-containing pharmaceutical compositions described above, would additionally include a quantity of a receptor antagonist to benzodiazepines. Such a receptor antagonist would begin counteracting the effect of benzodiazepine after the surgical procedure is complete, in essence providing a slow release feature. A non-limiting example of this antagonist is flumazenil also known under trade names such as ANEX-ATE®, ROMAZICON® and others. The use of antagonists is also envisioned as a routine practice (i.e., not just for sensitive patients), for example, in situations when a larger than typical or usual dosage of benzodiazepines is medically indicated, or recommended, or necessary. In some further applications, benzodiazepine-based compounds may be used in combination with non-benzodiazepine based sedatives such as eszopiclone, ramelteon, zolpidem, or zaleplon.

The second pharmaceutically active compound that is used in such compositions is an NMDA antagonist, as defined hereinabove, or pharmaceutically acceptable salts, hydrates, solvates or N-oxides thereof. One particular second pharmaceutically active compound that can be used in pharmaceutical compositions described and claimed herein is ketamine. Other specific, non-limiting examples of NMDA antagonists that can be used include dextrorphan, etomidate, methadone, memantine, amantadine and dextromethorphan. Each of these is also known under one or several trade names as shown in Table 2, which also discloses chemical names of such compounds. Those having ordinary skill in the art can select alternative suitable NMDA antagonists for using in the compositions, if so desired.

NSAID(s) may be so used in addition to, or instead of, β-blocker(s), and/or antiemetic(s). In a further aspect, the third pharmaceutically active compound may also include an antihistamine medicament, as defined hereinabove. Non-limiting examples of specific antihistamine medicaments that can be so used include, but are not limited to, any of hydroxyzine pamoate, hydroxyzine hydrochloride, diphenhydramine hydrochloride, meclizine, chlorpheniramine, clemastine, promethazine, or prochlorperazine, or any combi-

TABLE 2

Examples of NMDA Antagonists That Can Be Used in Compositions

| Compound | Chemical Name (IUPAC) | Trade Name(s) |
|---|---|---|
| Ketamine | 2-(2-chlorophenyl)-2-(methylamino)cyclohexanone | KETANEST ®, KETASET ®, KETALAR ® (HCl salt) |
| Dextrorphan | 17-methyl-9a,13a,14a-morphinan-3-ol | None |
| Etomidate | Ethyl-3-[(1R)-1-phenylethyl]imidazole-5-carboxylate | AMIDATE ®, HYPNOMIDATE ® |
| Methadone | 6-(dimethylamino)-4,4-diphenylheptan-3-one | DOLOPHINE ®, AMIDONE ® and others |
| Memantine | 3,5-dimethyladamantan-1-amine | AKATINOL ®, NAMENDA ® and others |
| Amantadine | Adamantan-1-amine | SYMMETREL ® |
| Dextromethorphan | (4bS,8aR,9S)-3-methoxy-11-methyl-6,7,8,8a,9,10-hexahydro-5H-9,4b-(epiminoethano)phenanthrene | ROBITUSSIN ®, DELSYM ® and others |

The therapeutically effective quantity of the NMDA antagonist(s) in the entire pharmaceutical composition can be between about 1.0 mass % and about 10.0 mass % of the composition. In some embodiments, the therapeutically effective amount of the NMDA antagonist(s) can be between about 4.0 mass % and about 6.0 mass %, for example, about 5.0 mass % of the composition. Accordingly, in various embodiments, the combined quantities of both the benzodiazepine-based compound(s) and the NMDA antagonist(s), taken together, in the entire pharmaceutical composition can be between about 1.2 mass % and about 15.0 mass % of the composition, such as between about 3.0 mass % and about 12.0 mass %, for example, about 10.0 mass % of the composition.

As mentioned above, the compositions may further optionally include at least one third pharmaceutically active compound. In such embodiments, the third pharmaceutically active compound is a β-blocker, as defined hereinabove, or pharmaceutically acceptable salts, hydrates, solvates or N-oxides thereof, or alternatively, and α-2-adrenergic agonist or, as another alternative, a pain reliever. In addition to, or instead of, β-blockers, the third pharmaceutically active compound may also include an antiemetic medicament, as defined hereinabove, or pharmaceutically acceptable salts, hydrates, solvates or N-oxides thereof.

In yet another aspect, the third pharmaceutically active compound may include one or several non-steroid anti-inflammatory drug(s) (NSAIDs), as defined hereinabove.

nation thereof. Again, antihistamine medicaments may be used in addition to, or instead of, any of the above-mentioned compounds that may be used as the third pharmaceutically active compound.

The therapeutically effective quantity of the third pharmaceutically active compound(s) in the entire pharmaceutical composition can be between about 0.1 mass % and about 5.0 mass % of the composition. In some embodiments, the therapeutic effective amount of the third pharmaceutically active compound(s) can be between about 1.0 mass % and about 4.0 mass %, for example, about 2.5 mass % of the composition.

One particular β-blocker that can be used as the third pharmaceutically active compound in pharmaceutical compositions described and claimed herein is metoprolol. Other specific, non-limiting examples of β-blockers or α-2-adrenergic agonists or pain relievers that can be used include, propranolol, acebutolol, nadolol, atenolol, betaxolol, esmolol, bisoprolol fumarate, carvedilol, nebivolol, penbutolol, timolol, sotalol, dexmedetomidine hydrochloride, and acetaminophen. Each of these is also known under one or several trade names as shown in Table 3, which also discloses chemical names of such compounds. Those having ordinary skill in the art can select alternative suitable β-blockers for using in the compositions, if so desired.

TABLE 3

Examples of β-Blockers That Can Be Used in Compositions

| Compound | Chemical Name (IUPAC) | Trade Name(s) |
|---|---|---|
| Metoprolol | 1-(isopropylamino)-3-[4-(2-methoxyethyl)phenoxy]propan-2-ol | LOPRESSOR ®, TOPROL ® |
| Propranolol | 1-(1-methylethylamino)-3-(1-naphthyloxy)propan-2-ol | CIPLA ®, INDERAL ® and many others |

TABLE 3-continued

Examples of β-Blockers That Can Be Used in Compositions

| Compound | Chemical Name (IUPAC) | Trade Name(s) |
|---|---|---|
| Acebutolol | N-{3-acetyl-4-[2-hydroxy-3-(propan-2-ylamino) propoxy]phenyl}butanamide | SECTRAL ®, PRENT ® |
| Nadolol | 5-{[3-(tert-butylamino)-2-hydroxypropyl]oxy}-1,2,3,4-tetrahydronaphthalene-2,3-diol | CORGARD ® |
| Atenolol | 2-{4-[2-hydroxy-3-(propan-2-ylamino)propoxy] phenyl}acetamide | TENORMIN ® |
| Betaxolol | 1-{4[2-(cyclopropylmethoxy)ethyl]-phenoxy}-3-(isopropylamino)propan-2-ol | KERLONE ®, BETOPTIC ® and others |
| Esmolol | 3-{4-[2-hydroxy-3-(propan-2-ylamino)propoxy] phenyl}propanoate | BREVIBLOC ® |
| Bisoprolol fumarate | 1-[4[[2(1-methylethoxy)ethoxy]methyl]phenoxy]-3[(1-methylethyl)amino]-2-propanol-2-butenedioate | ZEBETA ® |
| Carvedilol | 3-(9H-carbazol-4-yloxy)-2-hydroxypropyl-2-(2-methoxyphenoxy)ethylamine | COREG ®, CARVIL ® and many other |
| Nebivolol | 2,2'-azanediylbis(1-(6-fluorochroman-2-yl)ethanol) | NEBILET ®, BYSTOLIC ® |
| Penbutolol | 1-(tert-butylamino)-3-(2-cyclopentylphenoxy)propan-2-ol | LEVATOL ®, LEVATOLOL ® and many others |
| Timolol | 1-(tert-butylamino)-3-[(4-morpholin-4-yl-1,2,5-thiadiazol-3-yl)oxy]propan-2-ol | TIMOPTIC ®, BETIMOL ® and many others |
| Sotalol | N-{4-[1-hydroxy-2-(propan-2-ylamino)ethyl]phenyl} methanesulfonamide | BETAPACE ® and others |

One particular antiemetic that can be used as the third pharmaceutically active compound in pharmaceutical compositions described and claimed herein is ondansetron. Other specific, non-limiting examples of antiemetics that can be used include dolasetron, granisetron, palonosetron, promethazine, imenhydrinate, and meclizine. Each of these is also known under one or several trade names as shown in Table 4, which also discloses chemical names of such compounds. Those having ordinary skill in the art can select alternative suitable antiemetics for using in the compositions, if so desired.

Therefore, in various embodiments, the combined quantities of all the pharmaceutically active compounds (i.e., the benzodiazepine-based compound(s), the NMDA antagonist(s), the β-blocker(s)), and/or the antiemetic(s) taken together, in the entire pharmaceutical composition can be between about 1.3 mass % and about 20.0 mass % of the composition, such as between about 3.0 mass % and about 12.0 mass %, for example, about 10.0 mass % of the composition. Those having ordinary skill in the art will determine the most appropriate quantities of each the pharmaceutically active compound that are within the above-mentioned ranges and that are most suitable for a particular patient. As a non-limiting guideline only, the following mass ratios between the pharmaceutically active compounds may be used (Table 5) for compositions where the benzodiazepine-based compound is midazolam, the NMDA antagonist is ketamine hydrochloride and the β-blocker is propanolol hydrochloride:

TABLE 4

Examples of Antiemetics That Can Be Used in Compositions

| Compound | Chemical Name (IUPAC) | Trade Name(s) |
|---|---|---|
| Ondansetron | (RS)-9-methyl-3-[(2-methyl-1H-imidazol-1-yl)methyl]-2,3-dihydro-1H-carbazol-4(9H)-one | ZOFRAN ®, ONIDISOLV ® |
| Dolasetron | (2α,6α,8α,9aβ)-octahydro-3-oxo-2,6-methano-2H-quinolizin-8-yl-1H-indole-3-carboxylate monomethanesulfonate, monohydrate | ANZEMET ® |
| Granisetron | 1-methyl-N-((1R,3r,5S)-9-methyl-9-azabicyclo[3.3.1]nonan-3-yl)-1H-indazole-3-carboxamide | KYTRIL ® |
| Palonosetron | (3aS)-2-[(3S)-1-azabicyclo[2.2.2]oct-3-yl]-2,3,3a,4,5,6-hexahydro-1H-benz[de]isoquinolin-1-one | ALOXI ® |
| Promethazine | (RS)-N,N-dimethyl-1-(10H-phenothiazin-10-yl)propan-2-amine | PHENERGAN ® |
| Dimenhydrinate | 2-benzhydryloxy-N,N-dimethylethanamine;8-chloro-1,3-dimethyl-7H-purine-2,6-dione | DRAMAMINE ®, GRAVOL ®, VOMEX ®, many others |
| Meclizine | (RS)-1-[(4-chlorophenyl)(phenyl)methyl]-4-(3-methylbenzyl)piperazine | BONINE ®, BONAMINE ®, ANTIVERT ®, many others |

TABLE 5

Exemplary Mass Ratios between Midazolam, Ketamine Hydrochloride and Propanolol Hydrochloride in the Compositions

| Ratios | Midazolam | Ketamine Hydrochloride | Propanolol Hydrochloride |
|---|---|---|---|
| Between about | 1 | 2 | 1 |
| and about | 1 | 10 | 1 |
| Such as between about | 1 | 4 | 1 |
| and about | 1 | 6 | 1 |
| For example | 1 | 5 | 1 |

In one specific embodiment, which is exemplary and non-limiting, for the composition having midozalam as the first pharmaceutically active compound, ketamine as the second pharmaceutically active compound and ondansentron at the third pharmaceutically active compound, the mass midazolam:ketamine:odansentron ratio may be about 3:25:2.

The pharmaceutical compositions described herein may contain not only pharmaceutically active components but also, in some embodiments, may further include one or several inactive, neutral compounds which can be pharmaceutically acceptable excipient(s) or carrier(s), including, but not limited to, binder(s), antioxidant(s), adjuvant(s), synergist(s) and/or preservative(s). The mass concentration of such inactive compounds can be between about 80 mass % and about 99 mass % of the entire pharmaceutical composition, such as between about 85 mass % and about 95 mass %, e.g., about 90 mass %.

Some embodiments of the invention are directed to pharmaceutical formulations that are formulated as solid articles suitable for sublingual or oral administration, such as troches, lozenges, capsules, pills, caps or boluses. These solid compositions typically comprise binder(s) and/or excipient(s). They can be prepared by first mixing the pharmaceutically active compounds described above with suitable binder(s) and/or excipient(s) followed by molding or compressing the blend. Both hard and chewable lozenges and troches are within the scope of the invention.

Typical binder(s) that can be used for fabricating solid articles mentioned above include, without limitation, polyglycols as defined above, such as, e.g., polyethylene glycols (PEGs), polyethylene oxides (POE), methoxypolyethylene glycols, polypropylene glycols, polybutylene glycols or derivatives thereof having a molecular weight that is sufficient to provide the necessary hardness and time for dissolution of the troche; for example, the acceptable molecular weight can be within the range of between about 1,000 Daltons and about 8,000 Daltons. In some embodiments PEG-1450 or PEG-400 can be used. Non-limiting examples of some specific polyglycol derivatives that can be used are:

(a) PEG-laureates and dilaureates (e.g., PEG-10-, PEG-12-, PEG-20-, PEG-32-laurates, PEG-20- and PEG-32-dilaurates, PEG-20-glyceryl-, PEG-30-glyceryl- and PEG-40-glyceryl-laurates, PEG-80-sorbitan laurate);

(b) PEG-oleates, dioleates and trioleates (e.g., PEG-12-, PEG-15-, PEG-20-, PEG-32, PEG-200- and PEG-400-oleates, PEG-20- and PEG-32-dioleates, PEG-20-trioleate, PEG-25-glyceryl trioleate, PEG-20-glyceryl- and PEG-30-glyceryl-oleates, PEG-40-sorbitan oleate);

(c) PEG-stearates and distearates (e.g., PEG-15-, PEG-40-, PEG-100-stearates, PEG-32-distearate and PEG-20-glyceryl stearate)

(d) castor, palm kernel, corn and soya oil derivatives of PEG (e.g., PEG-35-, PEG-40- and PEG-60-castor oils, PEG-40-, PEG-50- and PEG-60-hydrogenated castor oils, PEG-40-palm kernel oil, PEG-60-corn oil, PEG-30-soya sterol);

(e) other PEG derivatives (e.g., PEG-24- and PEG-30-cholesterol, PEG-25-phytosterol, PEG-6- and PEG-8-caprate/caprylate glycerides, tocopheryl PEG-100 succinate, PEG-15-100 octylphenol products and PEG-10-100 nonylphenol products);

(f) other products such as polyglyceryl-10-laurate, POE-9- and POE-23-lauryl ethers, POE-10- and POE-20-oleyl ethers, POE-20-stearyl ether, polysorbates-20 and 80, polyglyceryl-10-oleate, Tween 40, Tween 60, sucrose monostearate, monolaurate and monopalmitate and various products of Poloxamer series.

Typical excipient(s) that can be used for fabricating solid articles mentioned above include, without limitation, gelatin, sodium saccharin, stevioside, peppermint oil, or any natural or artificial fruit, vegetable, flower, beverage or candy flavor.

As stated above, the compositions may optionally further comprise one or several antioxidant(s). If antioxidant(s) are used, non-limiting examples of those that can be used include α-tocopherol acetate, acetone sodium bisulfite, acetylcysteine, ascorbic acid, ascorbyl palmitate, butylated hydroxyanisole, butylated hydroxytoluene, cysteine, cysteine hydrochloride, tocopherol natural, tocopherol synthetic, dithiothreitol, monothioglycerol, nordihydroguaiaretic acid, propyl gallate, sodium bisulfite, sodium formaldehyde sulfoxylate, sodium metabisulfite, sodium sulfite, sodium thiosulfate, thiourea and tocopherols.

As stated above, the compositions may optionally further include one or several adjuvant(s) or synergists(s). If adjuvant(s) or synergists(s) are used, non-limiting examples of those that can be used include citric acid, EDTA (ethylenediaminetetraacetate) and salts, hydroxyquinoline sulfate, phosphoric acid and tartaric acid.

As stated above, the compositions may optionally further include one or several preservative(s). If preservative(s) are used, non-limiting examples of those that can be used include benzalkonium chloride, benzethonium chloride, benzoic acid and salts, benzyl alcohol, boric acid and salts, cetylpyridinium chloride, cetyltrimethyl ammonium bromide, chlorobutanol, chlorocresol, chorhexidine gluconate or chlorhexidine acetate, cresol, ethanol, imidazolidinyl urea, metacresol, methylparaben, nitromersol, o-phenyl phenol, parabens, phenol, phenylmercuric acetate/nitrate, propylparaben, sodium benzoate, sorbic acids and salts, β-phenylethyl alcohol and thimerosal.

The pharmaceutical formulation can be administered to a subject in need of conscious sedation, procedural sedation, analgesia and/or pre-sedation, and in general for any kind of non-general anesthesia, by various local administrations. More specifically, the pharmaceutical formulations described herein may be prescribed by ordinarily skilled medical practitioners such as physicians, as the means of conscious sedation or pre-sedation. This is intended to be used for certain patients who experience or expect to experience high anxiety, bouts of panic attacks, disquietude, apprehension, angst or similar feelings of psychological discomfort or distress prior to, or during, medical or surgical procedures as described in more detail below. The patients may be of any age, i.e., including children, adolescents and adults.

For example, the formulation can be used prior to various outpatient surgeries and medical procedures, both invasive and non-invasive, such as an ophthalmic surgery, outpatient medical or surgical procedures, dental procedures, urological procedures, obstetric and gynecological procedures, gastrointestinal procedures, otolaryngological procedures, cosmetic surgery procedures, dermatological procedures, podiatric procedures, orthopedic procedures, emergency medical treatments, psychiatric treatments, and veterinarian procedures.

Specific representative examples of the procedures that are amenable to use of the formulation include, without limitation, cataract surgery, glaucoma surgery, corneal surgery, eyelid surgery, retinal surgery, tooth extraction, oral surgery, root canal surgery, medical imaging procedures (e.g., MRI or CAT scanning, especially for patients suffering from claustrophobia), biopsy, bone marrow harvesting, colonoscopy, endoscopy and laparoscopy.

In one non-limiting embodiment, the local administration is by oral route, such as sublingually or buccally, typically being delivered to the patient via a solid delivery vehicle such as a troche, a lozenge, a capsule, a pill, a cap, and a bolus, as mentioned above. In an additional embodiment, the pharmaceutical composition may be formulated as a liquid item adapted for sublingual or buccal administration (in which case it will include all the pharmaceutically active compounds described above, but no pharmaceutically suitable binder); such liquid formulations may be delivered by any method to be selected by one having ordinary skill in the art of delivery of medications, e.g., via a syringe or a pipette. Such local administration may be used instead or intravenous administration or to complement the latter, as appropriate.

It will be understood by those having ordinary skill in the art that the specific dose level and frequency of dosage for any particular patient may be varied and will depend upon many factors including the activity of the specific compound employed, the metabolic stability and length of action of that compound, the age, body weight, general health, gender, diet and the severity of the particular condition being treated.

According to further embodiments, methods for fabricating the above-described pharmaceutical compositions are provided. A one-batch formulation method may be used, where the components of the pharmaceutical formulation can be combined in single container; the components may be added to the container simultaneously or consecutively. Alternatively, a two- or multiple-batch method(s) may be used if desired, where each component of the pharmaceutical formulation can be combined in separate container followed by combining the contents of each container.

In one exemplary, non-limiting procedure, pre-measured quantities of each ingredient in the form of dry powder can be mixed to form a dry blend followed by mixing it with a pre-molten troche base. The composition can then be molded to form a troche.

In additional embodiments, pharmaceutical kits are provided. The kit includes a sealed container approved for the storage of solid pharmaceutical compositions, the container containing one of the above-described pharmaceutical compositions an instruction for the use of the composition and the information about the composition are to be affixed to the container or otherwise enclosed with it.

The following examples are provided to further elucidate the advantages and features of the present invention, but are not intended to limit the scope of the invention. The examples are for the illustrative purposes only. USP pharmaceutical grade products were used in preparing the formulations described below.

Example 1. Preparing a Pharmaceutical Composition in the Form of a Troche

A pharmaceutical composition may be prepared as described below. The following products can be used in the amounts and concentrations specified:

(a) about 0.2 g of midazolam;
(b) about 2.0 g of ketamine hydrochloride;
(c) about 0.2 g of ondansetron hydrochloride;
(d) about 1 mL of lemon oil flavoring; and
(e) about 15.5 g of standard troche base (comprising polyglycol 1450, polyglycol 400, gelatin, sodium saccharin and steviaside).

The troche base can be melted at low heat while being stirred; when completely molten, the heat can be turned off with continued stirring. All the dry ingredients, pre-weighed can be added into the molten base followed by adding the flavoring and mixing all components together.

While any shape may be used, a half-moon shaped troche mold can be lightly sprayed with PAM® (or a suitable oil/releasing agent) to cover the entire surface of the mold and the mixture prepared as explained above can then be poured into the mold and allowed to cool and harden at room temperature. A heat gun can then be used to smooth out the surface followed by another round of cooling at room temperature followed by removing the so prepared troche from the mold, placing it into a prescription vial and labeling the vial. The troche is now ready to be administered.

Although the invention has been described with reference to the above examples, it will be understood that modifications and variations are encompassed within the spirit and scope of the invention. Accordingly, the invention is limited only by the following claims.

What is claimed is:

1. A pharmaceutical composition, comprising:
   (a) a therapeutically effective quantity of a first pharmaceutically active compound selected from the group consisting of midazolam, diazepam, lorazepam, flunitrazepam, alprazolam, chlordiazepoxide, clonazepam and clorazepate, and pharmaceutically acceptable salts, hydrates, solvates or N-oxides thereof, in combination with a non-benzodiazepine compound selected from the group consisting of eszopiclone, ramelteon, zolpidem, and zaleplon;
   (b) a therapeutically effective quantity of a second pharmaceutically active compound selected from the group consisting of ketamine, dextrorphan, etomidate, methadone, memantine, amantadine, dextromethorphan, and pharmaceutically acceptable salts, hydrates, solvates or N-oxides thereof;
   (c) a pharmaceutically suitable binder therefor; and
   (d) optionally, a pharmaceutically acceptable excipient,
   wherein the pharmaceutical composition is formulated as a solid item adapted for sublingual or buccal administration, the solid item being selected from the group consisting of a troche, a lozenge, a capsule, a pill, a cap and a bolus.

2. The pharmaceutical composition of claim 1, further comprising a therapeutically effective quantity of a third pharmaceutically active compound selected from the group consisting of β-blockers, antiemetic medicaments, NSAIDs, antihistamines, α-2-adrenergic agonists, pain relievers and combinations thereof, or pharmaceutically acceptable salts, hydrates, solvates or N-oxides thereof.

3. The pharmaceutical composition of claim 2, wherein the β-blocker, the α-2-adrenergic agonist or the pain reliever is selected from the group consisting of metoprolol, propranolol, acebutolol, nadolol, atenolol, betaxolol, esmolol, bisoprolol fumarate, carvedilol, nebivolol, penbutolol, timolol, sotalol, dexmedetomidine hydrochloride, and acetaminophen.

4. The pharmaceutical composition of claim 2, wherein the antiemetic medicament is selected from the group consisting of ondansentron, dolasetron, granisetron, palonosetron, promethazine, imenhydrinate, and meclizine.

5. The pharmaceutical composition of claim 2, wherein the NSAID is selected from the group consisting of bromfenac, ketorolac, etodolac, sulindac, diclofenac, aceclofenac, nepafenac, tolmetin, indomethacin, nabumetone, ketoprofen, dexketoprofen, ibuprofen, flurbiprofen, dexibuprofen, fenoprofen, loxoprofen, oxaprozin, naproxen, aspirin, salicylic acid, diflunisal, salsalate, mefenamic acid, meclofenamic acid, flufenamic acid, tolfenamic acid, meloxicam, piroxicam, ternoxicam, droxicam, lornoxicam, isoxicam, celecoxib, rofecoxib, valdecoxib, parecoxib, lumiracoxib, etoricoxib, firocoxib, nimesulide, clonixin, and licofelone.

6. The pharmaceutical composition of claim 2, wherein the antihistamine is selected from the group consisting of hydroxyzine pamoate, hydroxyzine hydrochloride, diphenhydramine hydrochloride, meclizine, chlorpheniramine, clemastine, promethazine, and prochlorperazine.

7. The pharmaceutical composition of claim 2, further comprising a therapeutically effective quantity of a receptor antagonist to benzodiazepines.

8. The pharmaceutical composition of claim 7, wherein the receptor antagonist is flumazenil.

9. The pharmaceutical composition of claim 2, wherein the first pharmaceutically active compound is midazolam, the second pharmaceutically active compound is ketamine and the third pharmaceutically active compound is metoprolol, wherein the medizolam:ketamine:metoprolol ratio is between about 1:2:1 and about 1:10:1 by mass.

10. The pharmaceutical composition of claim 2, wherein the first pharmaceutically active compound is midazolam, the second pharmaceutically active compound is ketamine and the third pharmaceutically active compound is ondansentron, wherein the midazolam:ketamine:ondansentron ratio is about 3:25:2 by mass.

11. The pharmaceutical composition of claim 1, wherein the solid item is a troche.

12. The pharmaceutical composition of claim 1, wherein the binder comprises a polyglycol or derivatives thereof having a molecular weight that is sufficient to provide suitable hardness and time for dissolution of the troche.

13. The pharmaceutical composition of claim 12, wherein the polyglycol is selected from the group consisting of polyethylene glycol, polyethylene oxide, methoxypolyethylene glycol, polypropylene glycol and polybutylene glycol.

14. The pharmaceutical composition of claim 13, wherein the excipient is selected from the group consisting of gelatin, sodium saccharin, stevioside, peppermint oil, any natural or artificial fruit, vegetable, flower, beverage or candy flavor, and combinations thereof.

15. The pharmaceutical composition of claim 1, wherein the binder comprises a product having a molecular weight that is sufficient to provide the necessary hardness and time for dissolution of the solid item, the binder being selected from the group consisting of methoxypolyethylene glycol, polypropylene glycol, polybutylene glycol, PEG-laureates, PEG-dilaureates, PEG-oleates, PEG-dioleates, PEG-trioleates, PEG-stearates, PEG-distearates, castor oil derivatives of PEG, palm kernel oil derivatives of PEG, corn oil derivatives of PEG, soya oil derivatives of PEG, cholesterol derivatives of PEG, phytosterol derivatives of PEG, caprate/caprylate glycerides derivatives of PEG, tocopheryl succinate derivatives of PEG, octylphenol derivatives of PEG, nonylphenol derivatives of PEG, polyglyceryl-10-laurate, polyglyceryl-10-oleate, POE-lauryl ethers, POE-oleyl ethers, POE-stearyl ethers, polysorbates, monostearate, monolaurate and monopalmitate derivatives of sucrose, and products of poly(oxypropylene)-co-poly(propylene oxide) family.

16. The pharmaceutical composition of claim 15, further comprising a therapeutically effective quantity of a third pharmaceutically active compound selected from the group consisting of β-blockers, antiemetic medicaments, NSAIDs, antihistamines, α-2-adrenergic agonists, pain relievers and combinations thereof, or pharmaceutically acceptable salts, hydrates, solvates or N-oxides thereof.

17. The pharmaceutical composition of claim 16, wherein the β-blocker, the α-2-adrenergic agonist or the pain reliever is selected from the group consisting of metoprolol, propranolol, acebutolol, nadolol, atenolol, betaxolol, esmolol, bisoprolol fumarate, carvedilol, nebivolol, penbutolol, timolol, sotalol, dexmedetomidine hydrochloride, and acetaminophen.

18. The pharmaceutical composition of claim 16, wherein the antiemetic medicament is selected from the group consisting of ondansentron, dolasetron, granisetron, palonosetron, promethazine, imenhydrinate, and meclizine.

19. The pharmaceutical composition of claim 16, further comprising a therapeutically effective quantity of a receptor antagonist to benzodiazepines.

20. The pharmaceutical composition of claim 19, wherein the receptor antagonist is flumazenil.

21. The pharmaceutical composition of claim 16, wherein the first pharmaceutically active compound is midazolam, the second pharmaceutically active compound is ketamine and the third pharmaceutically active compound is metoprolol, wherein the midazolam:ketamine:metoprolol ratio is between about 1:2:1 and about 1:10:1 by mass.

22. The pharmaceutical composition of claim 16, wherein the first pharmaceutically active compound is midazolam, the second pharmaceutically active compound is ketamine and the third pharmaceutically active compound is ondansentron, wherein the midazolam:ketamine:ondansentron ratio is about 3:25:2 by mass.

23. The pharmaceutical composition of claim 15, wherein the excipient is selected from the group consisting of gelatin, sodium saccharin, stevioside, peppermint oil, cherry flavor, lemon oil, raspberry flavor and combinations thereof.

* * * * *